United States Patent [19]
Shaibani

[11] Patent Number: 5,586,024
[45] Date of Patent: Dec. 17, 1996

[54] METHOD AND SYSTEM FOR THE DIAGNOSIS OF TRAUMA INJURIES

[76] Inventor: Saami J. Shaibani, 115 Winding Way Rd., Lynchburg, Va. 24502

[21] Appl. No.: 358,485

[22] Filed: Nov. 14, 1994

[51] Int. Cl.⁶ ...................................... A61B 5/02
[52] U.S. Cl. ...................................... 364/413.02
[58] Field of Search ................. 364/413.02, 413.03, 364/413.04, 413.05, 413.06; 128/696, 700

[56] References Cited

U.S. PATENT DOCUMENTS 4,489,387 12/1984 Lamb et al. .......................... 364/514

Primary Examiner—William E. Kamm
Assistant Examiner—Scott M. Getzow
Attorney, Agent, or Firm—Henderson & Sturm

[57] ABSTRACT

A system and method for the diagnosis of trauma injuries. The system utilizes a computer which includes a display monitor, a keyboard, printer, hard drive and a data base of accident records. Each of the accident records includes a set of accident factors and sustained injuries. In a preferred embodiment, the system utilizes a software program. The system prompts a user to input relevant information relating to the accident factors of a particular patient. The system then compares the entered patient accident factors to the accident factors of each record of the data base. If a substantial match between the two sets of accident records occurs, the system adds the sustained injuries listed in the data base record to a possible injury list. By comparing the entered patient accident factors to all records in the data base, a comprehensive list of possible injuries can be prepared.

16 Claims, 10 Drawing Sheets

RESQME 1.14B                    06/16/94 19:50

Welcome to RESQME

Ranked Evaluation of Symptoms
for Quality Management in the ER

Version 1.14B

Press [ENTER] to continue

[F1] help

*Fig. 4*

RESQME 1.14B                    06/16/94 19:50

UTILITY REQUIRED

1. Identify possible trauma
2. Update diagnosed trauma
3. Configure system

Type desired # and press [ENTER]:   1

[F1] help

*Fig. 5*

RESQME   1.14B                              06/16/94  19:50

> # TRAUMA EVENT
>
> 1. Automotive
> 2. Industrial
> 3. Domestic
> 4. Recreational
>
>
> Type desired # and press [ENTER] :    1

[F1] help

*Fig. 6*

RESQME   1.14B         #153495         06/16/94  19:50

> # OCCUPANT DETAILS
>
> | GENDER: | F / M / ? | M |
> |---|---|---|
> | AGE: | # of years | 50 |
> | HEIGHT: | # of ft., in. | 5, 10 |
> | WEIGHT: | # of pounds | 180 |
>
> Type value and press [ENTER] for each field

[F1] help   [F2] prev   [F3] next   [F4] end   [F5] new   [esc] more

*Fig. 7*

RESQME  1.14B      #153495      06/16/94 19:51

SEATING POSITION

1. Front left       6. Rear right
2. Front center     7. Thrid row left
3. Front right      8. Thrid row center
4. Rear left        9. Thrid row right
5. Rear center      10. Other Type desired # and press [ENTER] :    1

[F1] help  [F2] prev  [F3] next  [F4] end  [F5] new  [esc] more

*Fig. 8*

RESQME  1.14B      #153495      06/16/94 19:51

RESTRAINT USE

ADULT:    None / Lap / Shoulder / Both    B
INFANT:   Rearward / Forward
OTHER:    Child seat / Booster cushion
AIRBAG:   No / Yes / Unknown              N Type value and press [ENTER] for each field

[F1] help  [F2] prev  [F3] next  [F4] end  [F5] new  [esc] more

*Fig. 9*

RESQME 1.14B     #153495     06/16/94 19:51

VEHICLE DETAILS

1. VIN known         5. Intermediate
2. Year, make, model 6. Full size
3. Subcompact        7. Pickup truck
4. Compact           8. Other Type desired # and press [ENTER]:    3

[F1] help  [F2] prev  [F3] next  [F4] end  [F5] new  [esc] more

*Fig. 10*

RESQME 1.14B     #153495     06/16/94 19:51

IMPACT ANGLE

1. Frontal: offset right   8. Left side: rear
2. Right side: front       9. Left side: center
3. Right side: center     10. Left side: front
4. Right side: rear       11. Frontal: offset left
5. Rear end: offset right 12. Frontal: center
6. Rear end: center       13. Rollover
7. Rear end: offset left  14. Other Type desired # and press [ENTER]:    9

[F1] help  [F2] prev  [F3] next  [F4] end  [F5] new  [esc] more

*Fig. 11*

RESQME 1.14B     #153495     06/16/94 19:52

IMPACT SEVERITY

1. Minor     ( < 10 mph )
2. Moderate     ( 10-20 mph )
3. Serious     ( 20-30 mph )
4. Severe     ( > 30 mph )
5. Other Type desired # and press [ENTER] :    2

[F1] help    [F2] prev    [F3] next    [F4] end    [F5] new    [esc] more

*Fig. 12*

RESQME 1.14B     #153495     06/16/94 19:52

SUPPLEMENTARY DATA

Note any observed trauma and press [ENTER], then state location of MVA and press [ENTER]

LOC; lacerations to face; minor bleeding
Route 29

[F1] help    [F2] prev    [F3] next    [F4] end    [F5] new    [esc] more

*Fig. 13*

```
RESQME   1.14B           #153495            06/16/94 19:52
```

SUMMARY

| | | | |
|---|---|---|---|
| SEX: | Male | AGE: | 50 yrs |
| HEIGHT: | 5' 10" | WEIGHT | 180 lbs |
| SEATING: | Front left | BELT: | Lap-Shoulder |
| AIRBAG: | No | VEHICLE: | Subcompact |
| ANGLE: | Left side: center | DAMAGE: | Moderate |
| NOTES: | LOC; lacerations to face; minor bleeding | | |
| SITE: | Route 29 | | |

If correct, press [ENTER]

[F1] help   [F2] prev   [F3] next   [F4] end   [F5] new   [esc] more

*Fig. 14*

```
RESQME   1.14B           #153495            06/16/94 19:52
```

POSSIBLE DIAGNOSES 1. closed head injury          72 %
2. fracture of left ilium      35 %
3. thoracic soft tissue        14 %
4. dislocation of left hip     < 5 %
5. fracture of left rib(s)     < 5 %
6. abdominal soft tissue       < 5 %

Press [ENTER] to print above with summary

[F1] help   [F2] prev   [F3] next   [F4] end   [F5] new   [esc] more

*Fig. 15*

METHOD AND SYSTEM FOR THE DIAGNOSIS OF TRAUMA INJURIES

AUTHORIZATION PURSUANT TO 37 CFR 1.71 (d)(e)

A portion of the disclosure of this patent document may contain material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

The present invention relates generally to computer diagnostic systems and methods and specifically to a computer diagnostic system and method for assisting in the diagnosis of trauma injuries and more specifically in the diagnosis of trauma injuries sustained in automobile accidents.

BACKGROUND ART

The first sixty minutes after a trauma injury event has been referred to as the "golden hour." This hour immediately subsequent to the injury is critical in terms of getting the victim to an emergency room, diagnosing injuries and beginning treatment and management. Many factors work against the efficient use of this first hour. Often it takes significant time to transport the victim to the hospital. Once at the hospital, diagnosis must begin and often involves numerous tests. This process is frequently slowed by the condition of the victim. For example, if the victim is unconscious, then input from the patient regarding pain and the like cannot be obtained.

During the diagnosis stage, some injuries are obvious due to the physical manifestations involved in the symptoms. These physical manifestations include swelling, bruising, bleeding and perhaps misalignment of bones or body parts. However, some injuries are best classified as internal, typically in the chest area or in the head. These injuries may be simultaneously invisible and considerably more severe than any visible injury. These can be extremely dangerous injuries. With time a critical element, these types of injuries can easily be missed or overlooked during the initial examination and treatment.

In practice, the danger of missed or overlooked diagnosis is reduced by the experience of the diagnosing physician When a victim arrives having suffered a particular type of traumatic accident, an experienced physician attempts to narrow the scope of possible injuries based upon the anecdotal experiences of previously treated victims. The value of this approach is significant. However, the sum of a physician's experience is always modest when compared to the total number of serious accidents which occur and are treated by all physicians year after year. Another problem with this method arises when some indicative factors of a given trauma event are ignored at the expense of some less meaningful factors.

For example, in the area of automobile accidents, a physician in an emergency room certainly has seen a great deal of victims injured in automobile accidents. Additionally, the physician may be able to ascertain certain details about the accident, compare it to previous experiences, and improve the chances that a correct diagnosis can occur quickly. However, the physician, no matter how experienced, cannot master the extremely large number of permutations which can occur when several factors are involved. For example, it would be hard for a physician to practically know the difference between an accident in which the right rear quarter panel was hit at 25 miles per hour from an accident in which the car was hit in the same position but at 40 miles per hour. The problem is further compounded when factors such as vehicle type, victim information, seating position and restraint use are factored in.

The information needed to distinguish the subtle differences of accident factors is either available or could be compiled. However, in the golden hour of medical treatment, there is not enough time to compile or digest the necessary information. The problem is compounded when a traumatic event occurs in which there is concurrently a large number of trauma victims.

There is therefore a need for a system and method for diagnosing trauma injuries in a consistent, efficient and methodical manner.

DISCLOSURE OF THE INVENTION

The present invention relates generally to computer diagnostic systems and methods and specifically to a computer diagnostic system and method for assisting in the diagnosis of trauma injuries and more specifically in the diagnosis of trauma injuries sustained in automobile accidents. The system and method of the present invention is designed to provide efficient and rapid assistance to physicians in the emergency rooms which are attempting to treat one or more victims of a traumatic event.

The system comprises a computer which could be virtually any computer on the market today. The computer includes a display and keyboard and could also include a mouse and a printer. A data base of accident records is accessible by the computer. The data base can either be stored in the computer's hard drive, stored on disks, either floppy or CD-ROM, which are inserted into the computer, or stored on or in a separate storage device such as an external hard drive or a hard drive connected via a server.

The system prompts a user to input specific information about the trauma event and the victim. This information is called the patient accident factors and can include height, weight, age and gender as well as specific information about the trauma event. For example, if the trauma event was an automobile accident then information such as vehicle type, speed, victim positioning, angle of impact and restraint use would be important. If the trauma event was some sort of fall, then information such as was the fall a free fall or down a set of steps, how far or how many steps, type of surface upon which the victim landed and location of impact on victim's body would be important.

Once all of the patient accident factors have been entered into the system, a data base of accident records is utilized. Each record in the data base includes accident factors and sustained injuries. The data base is a compilation of accident reports of actual injuries. The patient accident factors are compared to the accident factors in each accident record. If a substantial match between the two sets of accident factors occurs, the list of sustained injuries is added to a list of possible injuries. Thus, when all of the data base records have been reviewed, a comprehensive list of possible injuries is produced and can be displayed to the operator either on the display monitor connected to the computer used in the system, or by printout on a printer connected to the system, or both.

The system is also capable of keeping track of how often a particular injury is present as the system scans through the data base for matches. Thus by comparing the frequency of the occurrence of a particular injury to the total number of matches, a probability of injury can also be shown in conjunction with each injury. The system is also capable of recognizing the relative severity of each injury. By utilizing this severity in conjunction with the probability of injury, the system can help assist a physician in determining not only what injuries to look for but also the order in which to do so.

An additional feature of the system of the present invention allows the system to utilize a digest of the data base to supply a quicker initial diagnosis. Thus, a much less detailed possible injury list is initially displayed while the system compares the detailed accident factors to each record. The digest injury list is limited but virtually immediate whereas the complete record search may take a few minutes but will be more detailed and accurate.

Another feature of the present invention allows for a physician to include anecdotal information which can be displayed. For example, a particular physician may believe that a particular injury is likely to occur for a particular set of accident factors. The system can be configured to remind the operator of the system of this condition in addition to the injuries listed as a result of the record search.

Still another feature of the present invention is to make available recommended treatments for each of the possible injuries. Thus, after the list of possible injuries is displayed, the operator of the system could then select a particular injury and the system will give a recommended treatment or management. As with the list of injuries, the system can be supplemented with additional recommendations. Therefore, if a physician does not like a particular treatment that is displayed, the system can be modified to either display a different treatment or to display alternative treatments.

The design of the system is such that it will be valuable while treating a single patient but the value of the invention is particularly evident during a major traumatic event in which there are multiple victims. The system provides a method of systematic triage which helps to provide a priority in which to treat the patients. Additionally, the system provides a safety net in such adverse conditions when the time available for each victim or patient is limited. Additionally, the system can be used as an educational tool by providing such a large number of permutations of accident factors and conditions.

An object of the present invention is to provide a diagnostic system and method for diagnosing trauma injuries.

A further object of the present invention is to provide a diagnostic system and method for diagnosing various trauma injuries which utilizes various data bases comprised of sets of previous accidents.

Another object of the present invention is to provide a diagnostic system and method for diagnosing trauma injuries which have occurred in an automobile accident.

A further object of the present invention is to provide a diagnostic system and method for diagnosing trauma injuries which utilizes a data base comprised of previous automobile accidents.

Another object of the present invention is to provide a diagnostic system and method for diagnosing trauma injuries which allows a preliminary diagnosis which utilizes a digest of a data base comprised of previous automobile accidents.

Still another object of the present invention is to provide a diagnostic system and method for diagnosing trauma injuries which allows a preliminary diagnosis which utilizes a data base comprised of previous automobile accidents and which allows the data base to be supplemented by anecdotal cases.

Another object of the present invention is to provide a diagnostic system and method for diagnosing trauma injuries which could be used as a triage assistant in the case of a catastrophe and which also could be used as an educational tool.

Other objects, advantages, and novel features of the present invention will become apparent from the following detailed description of the invention when considered in conjunction with the accompanying drawings.

BRIEF DESCRIPTION OF THE DRAWINGS

FIGS. 4–15 are representative screen displays for entering data and displaying information for a system built in accordance with the present invention.

BEST MODES FOR CARRYING OUT THE INVENTION

Figure 1:
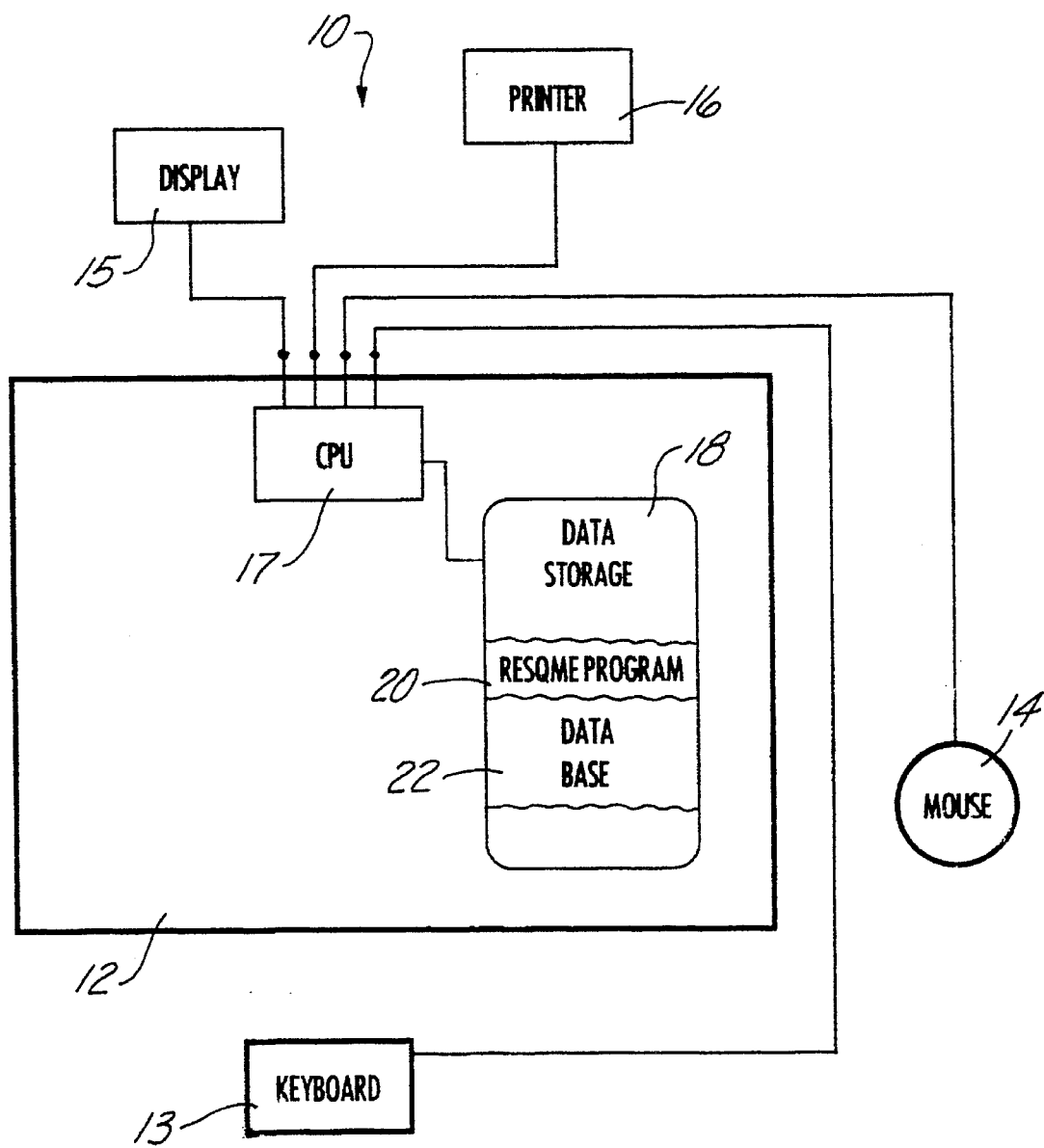
FIG. 1 is a symbolic representation of a system for diagnosing trauma injuries built in accordance with the present invention.

Referring now to the drawings wherein like reference numerals designate identical or corresponding parts throughout the several views, FIG. 1 shows symbolic representation of a system (10) for the diagnosis of trauma injuries built in accordance with the present invention. The system (10) includes a computer (12). The computer (12) could be virtually any computer on the market today such as an Intel 386, 486 or Pentium based computer, an Apple Macintosh either with a Motorola 68000 series processor or PowerPC processor or any other computer of similar or higher capabilities. The system (10) can utilize any computer but the computers listed above typically work better due to the faster nature of their operating speeds (25, 33, 50, 60, 75, 100 MHz and above). The system is also capable of working on larger mainframe computers though in a preferred embodiment the system would run on a stand alone PC.

The computer (12) includes a keyboard (13), a mouse (14), a display monitor (15), a printer (16), a CPU (17) and a disk drive (18) for operating system, data and program storage. The symbolic representation of the system (10) as shown in FIG. 1 is not meant to represent a complete computer, for example the RAM, video cards, internal buses, floppy disk drives, CD-ROM drives, etc. are not shown, but instead is meant to illustrate that virtually any computer with the traditional peripherals can be utilized in the system of the present invention.

The system utilizes a computer program (20) which in FIG. 1 is labeled the RESQME program. The system also utilizes a data base of accident records (22). Each accident record includes information relating to the circumstances surrounding the accident and the injuries sustained in the accident. The circumstances surrounding the accident are called accident factors. In a best mode embodiment, the data base will be a compilation of accident records involving a particular type of trauma event. For example, the data base essentially could be used in any situation in which a set of documented accidents is available. By establishing a large number of records, the system can analyze the records for patterns when given a certain set of accident factors. Additionally, the system provides a list of less likely but still potential injuries that are not frequent enough to be considered typical and therefore may be overlooked. Thus, the data base actually can be a compilation of several sets of accident records, each set relating to a particular type of accident. The system may only have one set, such as automobile accidents or it may have several sets, such as automobile accidents, industrial, domestic, recreational, and falling. From this point on, the discussion primarily will describe a trauma event relating to an automobile accident. This focus will occur for primarily two reasons. First, the automobile accident type trauma event provides a relatively familiar event in which to illustrate the use of the present invention. Second, the automobile accident is a trauma event for which there has been a great deal of documentation relating various accident factors to sustained injuries. For example, automobile accidents are nationally amassed in the National Accident Sampling System (NASS) and Fatal Accident Reporting System (FARS) data bases. However, it should be obvious that the following discussion of the use of the present invention does not in any way limit the use of the present invention to automobile accidents and that the scope of the present invention includes all types of traumatic accidents for which a set of injury records can be compiled.

The accident factors are a list of the factors which are most likely to be significant when determining the different injuries which could occur. Thus, in an automobile accident, the make and/or size of an automobile, the passenger position, the restraints used, the angle of impact and the speed at impact or impact severity are all very important, whereas the year of the car is not as important, and furthermore, whereas the color of the car is meaningless. These accident factors also include information about the victim of the accident such as gender, age, height and weight.

It is not necessary that the data base (22) be stored on the hard drive (18) of the computer (12). The data base (22) could be located anywhere so long as the computer was capable of accessing it when necessary. Accordingly, the data base (22) could be stored on one or more floppy disks which are inserted into the computer's disk drive. The data base could also be stored on CD-ROM which would be located in a CD-ROM drive connected to the computer. The data base could also be stored on an external hard disk either directly connected to the computer or connected via a network. Thus, the only important aspect is that the data base always be accessible to the computer.

Referring now to FIGS. 4–15, in a preferred embodiment of the present invention the system will always be loaded and running and will remain in an inactive state as shown in FIG. 4. When either a trauma event victim arrives at the emergency room or in the alternative when the information pertaining to the accident factors is available, either before or after the arrival of the victim, the user of the system will begin entering the relevant data or accident factors into the system. The system is designed to be menu driven. Additionally, as will be discussed in greater detail below, the system is flexible to allow the information to be entered in a variety of ways when appropriate.

Upon striking a key to commence the diagnosis system, the system will prompt or ask what type of function you wish to perform. This can be seen in FIG. 5. In the case of diagnosing a trauma injury, the operator of the system would select option 1, "Identify possible trauma." The operator could select the desired option either by entering the number 1 on the keyboard or by using the mouse to point to and select the desired option. In another embodiment of the present invention, a touch sensitive screen could be utilized such that the operator of the system could simply press on the desired option. In this embodiment, accommodations could be made such that the need for the keyboard could be eliminated by simultaneously providing the necessary key functions on the touch sensitive display screen.

Referring now to FIG. 6, the next screen prompts the user or operator for the particular type of trauma event which has occurred. Upon selection of the trauma event, the system prompts the user to input specific information regarding the victim. This is shown in FIG. 7. The information requested includes gender, age, height and weight of the victim.

The system is designed such that the greater the accuracy of the answers provided, the greater the accuracy of the diagnosis. However, it is understood that, in the environment in which the diagnosis system of the present invention will be used, perfect information will not always be available. Thus, the system will not require that all of the information be entered prior to moving on to the next screen. If a diagnosis is requested by the operator without fully providing all of the information, the system will utilize the information that has been provided and diagnose as accurately as possible with the limited information. Similarly, while actual values are preferred for greater accuracy in diagnosis, approximations are better than leaving the entry blank. For example, if the exact weight of a person is not known a guess which is within ten or fifteen pounds would be better than leaving the weight request blank. Similarly, information regarding specifics of the accident should be approximated as closely as possible if the exact information is not available.

In order to keep the operator of the system from providing incorrect or inappropriate information, the system includes a help function for each input screen. The help function provides an explanation of the type of information to be provided as well as how to approximate information that is unknown. For example, if the operator knows that the car was hit in the front end but does not know the speed at impact, the help function will provide guidance with how to estimate. The help function might say that if there are only scratches then the collision occurred at less than 10 miles per hour. Similarly it might say that if the damage to the front end of the vehicle was crushed inward greater than two feet, then the collision occurred at a speed greater than 30 miles per hour. Utilizing the help function ensures that more accurate information is entered into the system.

Referring now to FIGS. 8–12, following the specific information on the victim, specific information relating to the trauma event is requested. For the case of an automobile accident as shown in these figures, information involving the seating position, restraint use, vehicle details, impact angle and impact severity is requested. Referring now to FIG. 9, yet another method of entering data is shown. In addition to the methods described above, a distinct letter in each choice has been underlined. By pressing the underlined letter, that choice is automatically selected. If a different choice from the same category is selected, one of two possibilities occur. If the category is one in which only one answer is possible, then the second pressed option is taken. However, if the category is one in which the operator is to select all that apply, then both selections are taken. If the operator accidentally selects the wrong answer and wishes to remove it, then the operator simply presses the option again and it will be deselected. Thus, pressing the appropriate letter simply toggles that choice between selected and not selected.

Referring now to FIG. 13, after entering in all of the particular accident factors, supplementary data can be inserted which provides an opportunity to include necessary information for which there was no prompt. This type of information can include information specific to the patient such as a previous or preexisting condition, known negative reaction or susceptibilities to medication or treatment, observed trauma and the like.

Referring now to FIG. 14, the system provides the operator a summary of the information that has just been entered to ensure that the information is correct. At this point the operator either corrects mistaken information or requests that the system determine a list of possible diagnoses.

After all of the information has been correctly entered into the system, a comparison between the entered accident factors for the patient (or victim) and the accident factors listed in each record of the data base begins. As each record is compared, if there is a substantial match between the entered patient accident factors and the record accident factors, then the sustained injuries for that record are recorded in a possible injury list. The system continues this process until all of the records have been reviewed.

As the system compares each record in the data base it keeps track of the number of records which qualify as a substantial match. The system also keeps track of the number of occurrences of each type of injury. Utilizing the total number of matches and the frequency of a particular injury, a probability for each possible injury also can be determined. For example, if during the comparison of the patient accident factors to the records in the data base, the system generates 275 records with a substantial match, and of these 275 records 198 indicate a closed head injury, then the system would indicate a 72% probability (198/275* 100%). These probabilities help determine which injuries to search for first as well as providing a triage function when there are multiple patients. Additionally, the system can be designed to recognize the severity of each injury. Utilizing both this severity and the probability of occurrence, the order of trauma examination and triage functions are enhanced.

Even on some of the faster computers available on the market today, the process of comparing the patient accident factors to each of the records on the data base may take a few minutes. This is probable even utilizing various organization, classification and indexing strategies in the data base. Nevertheless, these strategies will improve the searching and comparison efficiency. Given that even a 3 minute delay is a 5% reduction of time during the first hour, the system can also use a representative digest of the data base to provide a virtually immediate preliminary diagnosis. The preliminary diagnosis is likely to only list one or two possible injuries but would be helpful during the few minutes of processing time for the full comparison.

Additionally, the system allows for the physician or hospital to add anecdotal examples to the data base. In one instance, the physician may find an injury which does not come up on the possible injury list. For example, perhaps the physician believes a particular injury occurred because the patient was riding in the back seat of the automobile. The physician can enter this information into the system and request that this injury be listed any time a victim has been riding in the back seat. In this case the injury will be included, regardless of whether or not that injury is found during the comparison with the data base.

In another instance, a hospital policy may require that a physician always check for a particular injury in a particular type of accident. This information can be entered into the system and will then always prompt the injury when that type of accident occurs. Additionally, the system could even be made to prompt an appropriate message that this injury must be checked.

Similar to prompting various messages associated with particular injuries, in one embodiment of the invention, the system could be used to recommend a treatment or management of an injury. Obviously the system cannot replace the expertise of the physician but it can be used as an assistant as well as a safety net when a large number of victims arrive in the emergency room at the same time.

Referring to FIG. 5, option 3 in this screen allows the operator to configure the system. The system is designed to be flexible such that it can be customized for each particular environment. The customization can involve anything from the relatively unimportant, such as the screen colors and selection of warning sounds, to the extremely important, such as the selection of the level of match required to constitute a substantial match and whether or not to display or make available treatment and management recommendations. Other customizations could include whether to automatically perform a digest analysis, whether to automatically provide anecdotal data, and determination of threshold levels.

Setting the level of the match is a critical feature of the present invention. For a match to be substantial, a predetermined level of correlation must be achieved. This can be important in an atypical case. If the correlation is defined too narrowly, too few records will match and the injury list will be limited. Additionally, with a small number of matches, the probabilities for each injury become less significant. Conversely, if the correlation level is too broad, then too many records create a match and too many possible injuries can be listed for practical use. One important factor in correlation setting revolves around the nature of the trauma event and the size of the data base. A very large data base allows for a narrower correlation. A smaller data base requires a larger correlation. Also, if the trauma event is relatively simple in terms of the number of permutations then a narrower correlation is appropriate. However, if a very large number of permutations are possible, then there may have to be a broader, more relaxed correlation.

Additionally, the problem of correlation setting is also not uniform. For example, a data base may have 500 records for males in the range of ages from 20 to 30 years. However the same data base may only have 10 records for women in excess of 80 years old. In this case, if the correlation level is very narrow, there still may be 20 or 25 matches for the 25 year old male. This would provide enough matches to satisfy a relatively accurate list of possible injuries in many cases. In the situation where an 83 year old woman is involved in the very same accident, there may only be 1 or zero matches. While one match would provide a list, it is not statistically as significant as a list derived from 20 or more matches.

Accordingly, the system is designed to accommodate various strategies to compensate for the correlation problem. It should be noted that no one strategy will be appropriate in all circumstances. Factors which influence the strategy have been discussed above and numerous other factors exist. Included in these other strategies is the way the system is perceived by the operator. If it is meant to provide the two or three most likely injuries then a narrow correlation is appropriate. Conversely, if the operator wishes to have as comprehensive list as possible then a wider or broader correlation is appropriate.

In one embodiment of the present invention, the threshold level can be adjusted. The threshold level contains two aspects. The first is a percentage level below which the injury is not going to be reported. For example, if the threshold level is 2% and a particular injury is only found in 1.45% of the records, then the injury will not be reported. Like the correlation level, the setting of this threshold level can be influenced by the way the operator views the system. If the operator wishes to obtain a list of every possible injury that has occurred the level would be set very low, such as 0%. On the other hand, if the operator reasons that there is not enough time to examine a patient for injuries which occur in less than 2% of the accidents of this type then the threshold should be set appropriately.

The second threshold is the level below which the differences in the percentages of occurrences are statistically insignificant. Referring to FIG. 15, a sample output of the system is shown. As can be seen in the injuries listed as 4, 5 and 6, each is listed with a probability of <5%. This indicates that the percentage is above the level at which they will not be reported but below a 5% threshold level. The 5% threshold level means that any injury which is to be listed but occurs less than 5% of the time will be listed as <5% instead of the actual percentage. This threshold level can either be set as a function of statistical significance or as a personal choice of the operator.

Obviously, the different configuration settings discussed above could be set in virtually an infinite number of ways. It is noted that these various setting combinations all fall within the scope of the presently disclosed invention and should be considered encompassed by the present invention.

Figure 2A:
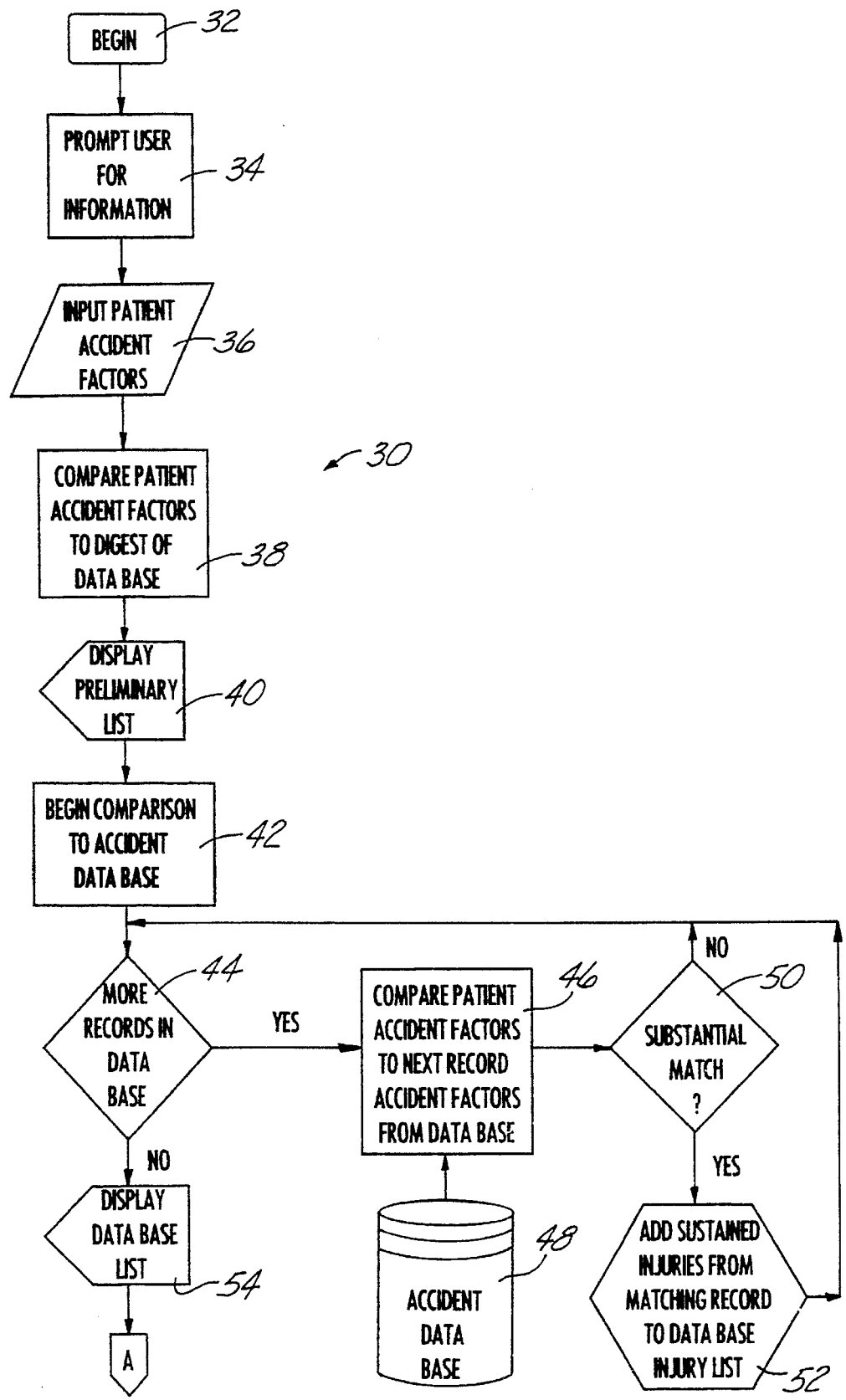
FIGS. 2A and 2B are flow chart diagrams detailing the method and system for diagnosing trauma injuries of the present invention.

Referring now to FIG. 2A, a flow chart (30) showing the basic function of the present invention is shown. Upon initiation (32), the system begins prompting the user for information or patient accident factors (34). The user then inputs the information pertaining to the victim or patient (36). If the system is configured to give a preliminary list of possible injuries, the system compares the entered patient accident facts to a digest of the data base (38) and then displays the preliminary list (40). The system then begins to do a full comparison with the entire data base (42).

The comparison with the data base is essentially a loop of determining if there are records remaining in the data base to be compared (44), if yes, comparing the next record (46) from the data base (48), determining if there is a substantial match or correlation (50), if yes, adding the sustained injuries to the list of injuries (52), then returning to determine if there are additional records remaining to be compared (44). If there is not a substantial match (50), then the system immediately loops back to determine if there are remaining records to be compared (44).

Figure 2B:
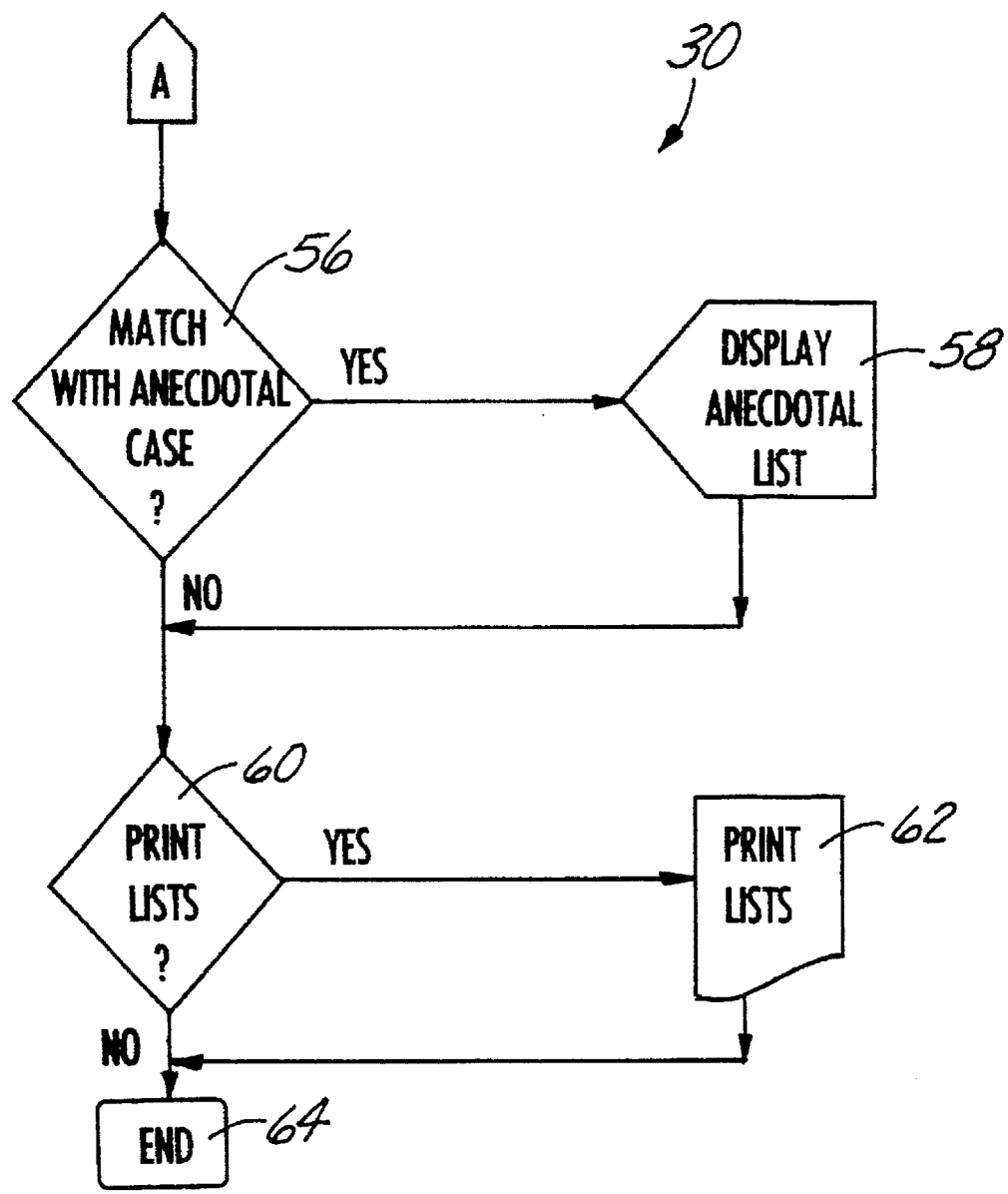

When there are no more records remaining to be compared (44), the system compiles and displays the list of possible injuries (54). Referring now to FIG. 2B, the system next determines if there is any relevant anecdotal data (56) and, if so, displays the anecdotal data (58). The display of anecdotal information assumes that the configuration of the system is such that anecdotal data is to be displayed. Finally, if the computer of the system includes a printer, the system can be configured to prompt the user (60) whether or not to print the different lists. If the operator selects yes, the configured or selected lists are primed (62). In addition to the possible injury lists, the patient information can be printed on the printout to avoid the possibility of one patient's list being used for a different patient. At this point the diagnosis is complete (64).

The system is capable of saving the patient information as well as the search results. This can be useful in the situation where more information is learned at a later time and a second diagnosis attempt is desired. The operator can simply recall the saved information and correct or supplement the earlier information without the need to re-enter the unchanged information.

Figure 3:
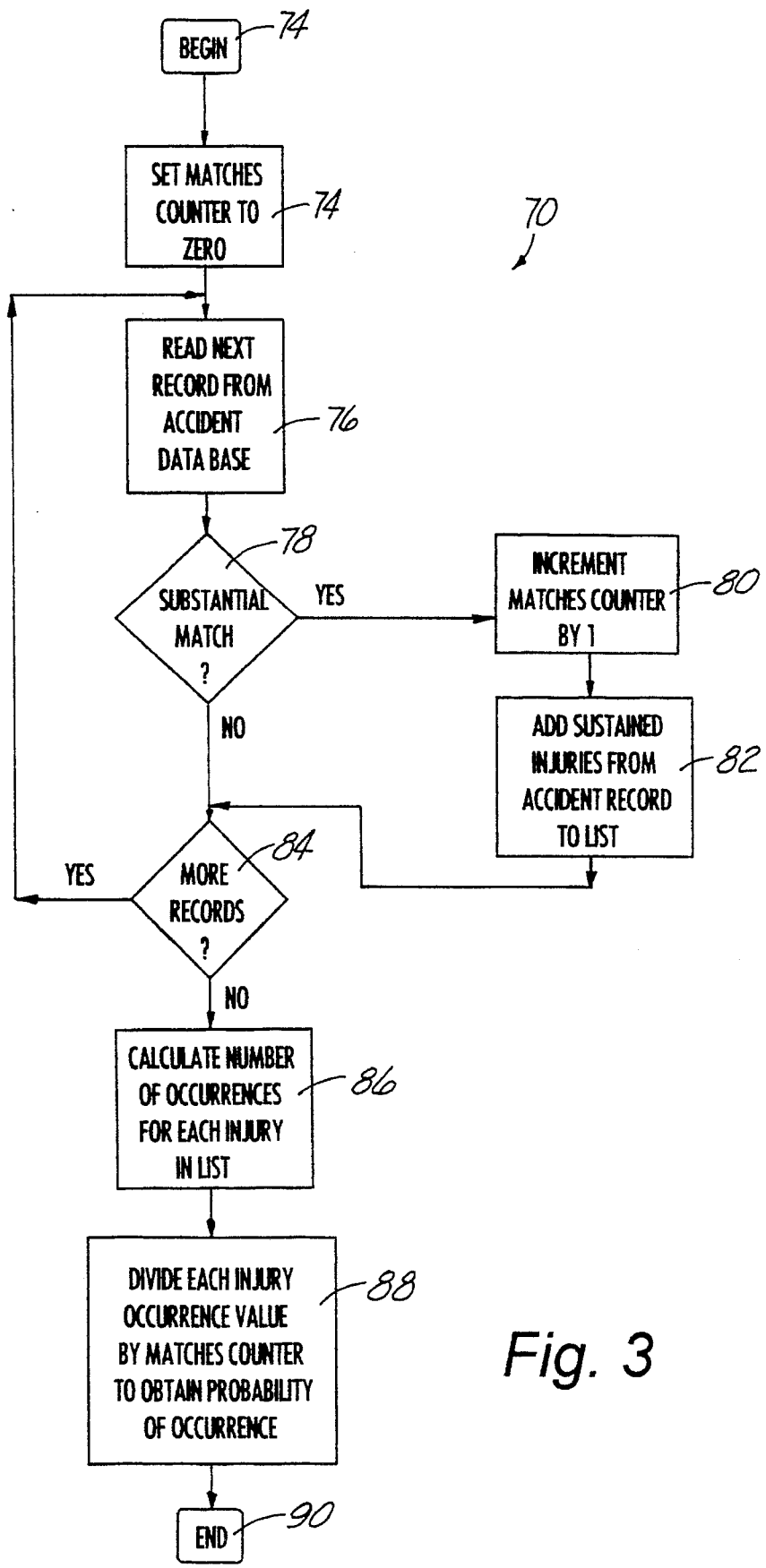
FIG. 3 is a flow chart diagram showing how injuries are added to the injury list and how probability of each injury is calculated.

Referring now to FIG. 3, a flow chart (70) detailing the comparison process is shown. At the beginning (72) of the comparison process a variable to keep count of the number of matches is set to zero (74). The first (or next) record is then retrieved from the data base (76). A comparison of the entered patient accident factors is made with the accident factors of the record from the data base to determine if there is a substantial match (78). If the match is substantial, then the counter keeping track of the matches is incremented (80). Next, the set of sustained injuries from the record is added to the injury list (82). Next, or if there was no substantial match, the system determines if there are more records remaining for comparison (84).

If there are additional records the system loops back to retrieve the next record (76). If not, the system begins to calculate the number of occurrences for each injury in the list (86). As a practical and efficient programming matter, this will probably be done as the injuries are added to the list (82). That is to say, when an injury is to be added to the list, the system will determine if that injury is already present in the list. If it is not, then the system will add it to the list and assign that particular injury a unique counter and will set that counter to one. If the injury is found in the list, then the system will simply increment its unique counter by one. Obviously, though not shown, the injury list must be wiped clean at the beginning of each entire data base comparison sequence (72).

Once the number of occurrences for each injury has been determined, a probability for each injury can be determined by dividing the number of occurrences by the total number of matches and multiplying by 100 percent.

Obviously, many modifications and variations of the present invention are possible in light of the above teachings. It is therefore to be understood that, within the scope of the appended claims, the invention may be practiced otherwise than as specifically described.

I claim:

1. A system for diagnosing trauma injuries, comprising:

a computer;

a data base, said data base comprising a set of accident records wherein each accident record includes accident factors and sustained injuries;

means for entering a set of patient accident factors wherein said entered patient accident factors are specific to a particular victim of a trauma injury event;

means for comparing said entered patient accident factors to the accident factors contained in each of said accident records in said data base;

means for developing a list of possible injuries wherein said list comprises the sustained injuries included from each record of said data base wherein the accident factors of a particular accident record in said data base substantially matches said entered patient accident factors; and means for displaying said list of possible injuries.

2. The system for diagnosing trauma injuries of claim 1 including means for determining the statistical likelihood of each injury listed in the list of possible injuries.

3. The system for diagnosing trauma injuries of claim 2 wherein said particular trauma event is an automobile accident.

4. The system for diagnosing trauma injuries of claim 2 including:

a digest of said data base; and means for determining a list of possible injuries based on a comparison between one or more of said entered patient accident factors and said digest of said data base.

5. The system for diagnosing trauma injuries of claim 3 wherein said accident factors include: age; gender; height; weight; seating position; restraint use; vehicle type; and impact information.

6. The system for diagnosing trauma injuries of claim 1 wherein said data base can be supplemented with anecdotal data.

7. The system for diagnosing trauma injuries of claim 1 wherein the displaying means includes a video monitor.

8. The system for diagnosing trauma injuries of claim 1 wherein the displaying means includes a printer.

9. The system for diagnosing trauma injuries of claim 1 including means for displaying a recommended treatment or management for each of said injuries on said list of possible injuries.

10. The system for diagnosing trauma injuries of claim 1 wherein said means for entering a set of patient accident factors includes means for prompting the operator of the system for relevant information.

11. A method of diagnosing trauma injuries utilizing a computer system comprising the steps:

entering accident factors specific to a particular victim of a trauma injury event;

comparing said entered patient accident factors to a data base comprised of accident records wherein each accident record includes accident factors and sustained injuries;

developing a list of possible injuries wherein said list comprises the sustained injuries included from each record of said data base wherein the accident factors of a particular accident record in said data base substantially matches said entered patient accident factors; and displaying said list of possible injuries.

12. The method of diagnosing trauma injuries utilizing a computer system of claim 11 including the step:

determining the statistical likelihood of each injury listed in the list of possible injuries.

13. The method of diagnosing trauma injuries utilizing a computer system of claim 11 including the steps:

comparing the entered patient accident factors to a digest of the data base; and displaying a preliminary list of possible injuries based upon a comparison of the digest of the data base and one or more of the entered patient accident factors.

14. The method of diagnosing trauma injuries utilizing a computer system of claim 11 including the step:

displaying a recommended treatment or management strategy for each of the injuries in said list of possible injuries.

15. The method of diagnosing trauma injuries utilizing a computer system of claim 11 including the steps:

supplementing the data base with anecdotal information wherein said anecdotal information includes its own record of accident factors and sustained injuries; and displaying said anecdotal information upon a substantial match of the supplemental record accident factors and the entered patient accident factors.

16. The method of diagnosing trauma injuries utilizing a computer system of claim 11 including the step:

prompting the user for relevant information during the entering of the patient accident factors.

* * * * *